United States Patent [19]

Ryan

[11] Patent Number: 4,906,457
[45] Date of Patent: Mar. 6, 1990

[54] COMPOSITIONS AND METHODS FOR REDUCING THE RISK OF SUNLIGHT AND ULTRAVIOLET INDUCED SKIN CANCER

[75] Inventor: Clarence A. Ryan, Pullman, Wash.

[73] Assignee: Washington State University Research Foundation, Inc., Pullman, Wash.

[21] Appl. No.: 241,039

[22] Filed: Sep. 6, 1988

[51] Int. Cl.⁴ .................. A61K 7/40; A61K 7/42; A61K 37/48
[52] U.S. Cl. .................... 424/59; 424/60; 424/94.1; 514/847; 514/937; 514/938; 514/939; 514/944; 514/969
[58] Field of Search ............................ 424/59

[56] References Cited

PUBLICATIONS

Rinne et al, Chem. Abs., 1980, vol. 92, 213629f.
Ohkoshi, Chem. Abs., 1982, vol. 96, 97304v.
Ohkoshi, Chem. Abs., 1984, vol. 100, 46760j.
Ohkoshi et al, Chem. Abs., 1984, vol. 101, 122650m.
Watanabe et al, Chem. Abs., 1987, vol. 107, 146970r.
Billings et al., "Inhibition of Radiation-Induced Transformation of C3H/10T½ Cells by Chymotrypsin Inhibitor 1 From Potatoes", Careinogenesis, vol. 8, No. 6, pp. 809-812.
Troll et al., "Tumorigenesis in Mouse Skin Inhibition by Synthetic Inhibitors of Proteases", Science, vol. 169, 18 Sep. 1970, pp. 1211-1213.
Hozumi et al., "Inhibition of Tumorigenesis in Mouse Skin by Leupeptin, a Protease Inhibitor from Actinomycetes", Cancer Research 32, Aug. 1972, pp. 1725-1728.

Primary Examiner—Dale R. Ore
Attorney, Agent, or Firm—Wells, St. John & Roberts

[57] ABSTRACT

Compositions and methods for reducing the risk of skin cancer. The novel compositions include at least one effective protease inhibitor. Preferred protease inhibitors include serine protease inhibitors and metallo- protease inhibitors. The protease inhibitors are preferably included in concentrations ranging from approximately 10 picograms to 10 milligrams per milliliter of the skin-applicable topical mixtures. The topical mixtures preferably include a suitable topical vehicle such as a cream, lotion, or ointment. One class of anti-carcinogenic skin treatment compositions of this invention preferably includes the desired protease inhibitors in combination with a suitable sunscreen agent or agents, such as para-amino benzoic acid, to provide particularly advantageous compositions for reducing the risk of sunlight-induced skin cancer.

22 Claims, No Drawings

COMPOSITIONS AND METHODS FOR REDUCING THE RISK OF SUNLIGHT AND ULTRAVIOLET INDUCED SKIN CANCER

TECHNICAL FIELD

The technical field of this invention is compositions and methods for treating skin to reduce the risk of skin cancer caused by sunlight or other sources of ultraviolet radiation.

BACKGROUND OF THE INVENTION

Skin cancer is a prevalent disease in humans caused by overexposure to ultraviolet radiation from the sun and other sources. It is commonly known that people with dark skin, or skin that easily tans, are less likely to develop skin cancer due to sunlight exposure. This reduced risk of sunlight-induced cancer is apparently due to the protective nature of melanin against ultraviolet light, and the relatively higher concentrations of melanin in the skin of darker skinned peoples. Current methods for reducing the risk of skin cancer caused by sunlight usually involve the control or elimination of sunlight exposure. Examples include mechanical blocking of the sun's rays, or chemical screening of the sun's rays, such as by using the ultraviolet sunscreen ingredient para-amino benzoic acid (PABA). Although such approaches appear to reduce the risk of sunlight and other ultraviolet radiation induced skin cancer, there remains a need for additional methods of treatment, particularly method which are effective for treatment after exposure to the ultraviolet light.

DETAILED DESCRIPTION OF THE PREFERRED EMBODIMENTS

The present invention includes the discovery that at least some types of protease inhibitors can be used in relatively minute concentrations to treat skin and thereby reduce the risk of skin cancer associated with exposure to sunlight. The protease inhibitors can be applied prospectively to interrupt or reverse the biochemical processes in the skin which are caused by sunlight or ultraviolet exposure and that lead to skin cancer. Retrospective application of the protease inhibitors is also effective in reducing the risk of skin cancer. Although the exact mechanism of action is not currently known, it is hypothesized that the protease inhibitors act to inhibit the production of, or the presence or activity of, at least certain types of protease enzymes (proteolytic enzymes) which are contributing factors in sunlight and ultraviolet induced skin cancer initiation. The inhibition or reduction of the protease enzymes, or their activities, reduces the likelihood that a tumorigenic reaction will occur in a cell, or that any tumorigenic reaction will not become effective to cause malignant cell reproduction. The action of the protease inhibitors thus reduce the overall likelihood and rate of sunlight-induced skin cancer in humans.

A variety of protease inhibitors are useful in this invention. Preferred classes of protease inhibitors useful in this invention include those that inhibit the serine class and the metallo-class of proteases. Inhibitors of cysteine and aspartyl proteases are also believed effective. The protease inhibitors useful in the invention generally include most or all known protease inhibitors derived from plants, animals or microorganisms, as well as synthetic protease inhibitors. Preferred types of serine protease inhibitors include the chymotrypsin and trypsin families of protease inhibitors derived from plants, such as from potatoes and soybeans. The soybean-derived Bowman Birk inhibitor family and the potato inhibitor 1 family are appropriate families of inhibitors for use in the novel compositions and methods of this invention. Also appropriate are inhibitors of elastase and other inhibitors of pancreatic proteolytic enzymes. Appropriate protease inhibitors from the metallo-class of protease inhibitors in particular include the carboxy-peptidase inhibitors. These and other protease inhibitors are commercially available and can be prepared using a variety of production techniques known in the art or hereafter developed The protease inhibitors used in the compositions and methods according to this invention are preferably included in amounts sufficient to provide effective inhibition of at least one of the proteases present in skin cells being treated. Concentrations as low as approximately 10 picograms per milliliter of applied topical mixture are believed effective to provide at least some reduction of the risk of sunlight-induced skin cancer. Protease inhibitor concentrations ranging from that value to approximately 10 milligrams per milliliter, or higher, in the applied topical mixture are believed effective and appropriate for use in the novel methods and compositions. More preferably, the active protease inhibitors are included in amounts sufficient to provide concentrations ranging from approximately 1 nanogram per milliliter to approximately 1 milligram per milliliter. Still more preferred are concentrations of approximately 0.1 milligrams per milliliter of topical mixture. Variations in the relative effectiveness of differing protease inhibitors cause the preferred concentrations to vary.

The compositions according to this invention preferably include the desired protease inhibitors in combination with one or more suitable topical ointments, creams, lotions or similar topical vehicles allowing for relatively even and dilute application of the active ingredient or ingredients to exposed surfaces of healthy skin. A variety of commercially available topical vehicles are appropriate for use in this invention. The topical vehicle should preferably be of a type which does not cause significant degradation of the protease inhibitors and any additives used in the skin treatment compositions of this invention. Topical vehicles suitable for use in this invention can be selected from water-in-oil and oil-in-water emulsions of mineral, vegetable, animal and synthetic oils; petrolatum; glycerol; mineral; vegetable, animal and synthetic oils; propylene glycol; other aliphatic and aromatic alcohols which can be tolerated by the skin and many other vehicles suitable for topical application to skin.

The compositions according to this invention can also be enhanced by including other suitable additives in the topical mixtures. One preferred class of anti-carcinogenic skin treatment compositions according to this invention uses a suitable protease inhibitor in combination with a suitable chemical sunscreen, in particular sunscreens which are effective at reducing the intensity of ultraviolet radiation which reaches the skin. Sunscreens which may be suitable for use in the novel skin treatment compositions include in particular para-amino benzoic acid (PABA). PABA is preferably included in the novel compositions in amounts sufficient to provide concentrations ranging from none to approximately 100 milligrams of PABA per milliliter of the topical anit-carcinogenic mixtures. Concentration of the ultraviolet screening agent in amounts sufficient to provide sunscreen factors ranging from approximately 1 to approximately 30 are also indicative of the concentration of PABA or other ultraviolet screening agent which may be included. Other sunscreens which do not cause significant degradation of the active protease inhibitors and which are tolerated by the skin are also suitable for use in this invention. Examples of additional sunscreens which may be useful include octyl dimethyl PBA, octyl salicylate, palmitate O, oxybenzone, and others. The PABA or other suitable ultraviolet screening agent or agents are advantageously included to provide a combined sunscreen and anti-carcinogenic effect which is particularly effective and easy to apply in a routine manner prior to or during exposure to sunlight.

A variety of other additives may also be included in skin treatment compositions according to this invention for a variety of purposes. Ingredients for enhancing or providing humectant properties, spreadability, non-greasiness, fragrance, absorbability and many other desirable attributes of the novel skin treatment compositions can also be included. Any such additive ingredients are preferably selected to be without deleterious effect on the particular protease inhibitors used and their stability within the particular skin treatment compositions.

The novel compositions are preferably made by selecting, buying or manufacturing a suitable cream, lotion, ointment or other topical vehicle and then mixing the desired active ingredient or combination of active ingredients into the vehicle in the desired proportions. The active ingredients include the desired protease inhibitors and any suitable ultraviolet screening agent. Any desired additional additives such as described above are also mixed into the topical mixture in the desired concentrations.

The invention also includes novel methods for treating skin to reduce the risk of skin cancer induced by sunlight or other source of ultraviolet radiation. The methods are useful in treating mammals, more particularly primates, especially humans, both male and female. The novel methods include obtaining or preparing a suitable anti-cancer cream or other composition, such as described hereinabove. The compositions are applied to the skin in amounts sufficient to create effective application rates from approximately 1 picogram to approximately 10 milligrams or higher of the active protease inhibitors per square centimeter of treated exposed skin area. The novel compositions are most preferably applied to healthy skin not opened by wound, disease or other affliction. The novel compositions are spread evenly onto the skin by the user's hands or with the aid of a suitable applicator, such as a brush, wand or other implement.

EXAMPLE 1

An anti-carcinogenic topical lotion according to this invention can be prepared by mixing 10 milliliters of U.S.P. grade glycerol into 40 milliliters of distilled water to produce a relatively homogeneous mixture. A suitable protease inhibitor, such as potato inhibitor 1, is then mixed into the glycerol and water mixture by slowly stirring the mixture and adding 5 milligrams of the potato inhibitor 1. The resulting glycerol, water and protease inhibitor mixture can be stored at room temperatures. The mixture is advantageously used in the manner typical of lotions by spreading a moist even layer over the user's skin and allowing it to be absorbed into the skin. The anti-carcinogenic mixture is preferably applied to the skin to produce applied surface concentrations of roughly 1 milliliter of lotion to 10 square centimeters of skin, to thus produce surface concentrations of the protease inhibitor roughly equal to 0.01 milligrams per square centimeter. The anti-carcinogenic mixture can be applied after exposure to ultraviolet rays to assist the reconstructive processes of any damaged cells and thereby reduce the risk of tumorigenesis.

EXAMPLE 2

A commercially available suntan lotion known by the brand name SEA AND SKI with sun protection factor of 6 is selected. The listed ingredients are: octyl dimethyl PBA and octyl salicylate as sunscreen agents; cyclomethicone, ethylcellulose, dimethicone, trimethylsiloxysilicate, and fragrance are listed as other ingredients. Into this suntan lotion is mixed the soybean-derived Bowman Birk inhibitor in amounts sufficient to produce concentrations of the protease inhibitor equal to 1 milligram per milliliter of suntan lotion. The resulting combination is mixed to homogeneity. The resulting anti-carcinogenic lotion is then applied to the skin in suitable amount such as roughly 1 milliliter per 10 square centimeters. The applied combination of sunscreen and protease inhibitor reduces exposure of the skin to ultraviolet rays and biochemically reduces the risk of ultraviolet-induced skin cancer.

EXAMPLE 3

Another commercially available suntan lotion sold under the brand name COPPERTONE-CREAM is selected. The cream has an indicated sun protection factor of 8. The listed ingredients include: palmitate O and oxybenzone as sunscreen agents; and sorbitansesquioleate, sorbitol, glyceryl stearate SE, isopropylmyristate, triethanolamine, octadecene/maleic anhydride copolomer, benzyl alcohol, lanolin, jajoba oil, cocoa butter, aloe extract, methylparaben, propylparaben, vitamin E acetate, fragrance, and water are listed as other ingredients. Into 50 milliliters of said lotion is mixed 1 milligram of commercially available elastase inhibitor. The constituents are mixed to homogeneity to produce protease inhibitor concentration of approximately 20 micrograms per milliliter of the anti-carcinogenic lotion. The lotion is then applied to the skin to reduce the risk of ultraviolet-exposure-induced skin cancer.

EXAMPLE 4

A commercially-available after sun lotion sold under the brand name HAWAIIAN TROPIC AFTER SUN MOISTURIZER CREAM was obtained. The listed ingredients included: mineral oil; propylene glycol; glycerol stearate; polyethylene glycol stearate; cetyl alcohol; triethanolamine; methylparaben; cocoa butter; hydrogenated vegetable oil; coconut oil; avocado oil; vitamin E acetate; extracts of mango, papaya, guava and passion fruit; and fragrance. Into 100 milliliters of the cream is mixed approximately 1 milligram of carboxy-peptidase inhibitor to the point of homogeneity. The resulting anti-carcinogenic after sun moisturizing cream is then applied in the usual fashion to moisturize the skin and reduce the risk of cancer caused by sunlight exposure.

I claim:

1. A topical composition for reducing the risk of skin cancer caused by sunlight or ultraviolet exposure, comprising:
   an effective amount of at least one protease enzyme inhibiting agent in amounts sufficient to effectively reduce a concentration of at least one proteolytic enzyme present in the skin to which said composition is being applied; and
   at least one suitable, non-carcinogenic topical vehicle selected from the group consisting of ointments, creams, lotions, emulsions, oils, and alcohols.

2. A composition according to claim 1 and further defined by said effective amount of at least one protease enzyme inhibiting agent being present in said composition in amounts sufficient to provide combined concentration thereof from approximately 10 picograms per milliliter of said composition to approximately 10 milligrams per milliliter of said composition.

3. A composition according to claim 1 and further defined by said effective amount of said at least one protease enzyme inhibiting agent being present in said composition in amounts sufficient to provide combined concentration thereof from approximately 1 nanogram per milliliter of said composition to approximately 1 milligram per milliliter of said composition.

4. A composition according to claim 1 wherein said effective amount of at least one protease enzyme inhibiting agent includes at least one protease enzyme inhibiting agent which is selected from the group consisting of: protease enzyme inhibitors of the serine class of proteases; protease enzyme inhibitors of the cysteine class of proteases; protease enzyme inhibitors of the aspartyl class of proteases; protease enzyme inhibitors of the metallo class of proteases; protease enzyme inhibitors of the carboxy-peptidase class of proteases; protease enzyme inhibitors of the trypsin class of proteases; protease enzyme inhibitors of the chymotrypsin class of proteases; protease enzyme inhibitors of the pancreatic proteases; protease enzyme inhibitors of the elastase class of proteases; protease enzyme inhibitors of the Bowman Birk inhibitor family; protease enzyme inhibitors of the potato inhibitor 1 family.

5. A composition according to claim 4 and further defined by said effective amount of at least one protease enzyme inhibiting agent being present in said composition in amounts sufficient to provide combined concentration thereof from approximately 10 picograms per milliliter of said composition to approximately 10 milligrams per milliliter of said composition.

6. A composition according to claim 4 and further defined by said effective amount of at least one protease enzyme inhibiting agent being present in said composition in amounts sufficient to provide combined concentration thereof from approximately 1 nanogram per milliliter of said composition to approximately 1 milligram per milliliter of said composition.

7. A composition according to claim 1 and further comprising at least one suitable ultraviolet sunscreen agent in amounts sufficient to reduce the amount of ultraviolet light striking skin treated with the composition.

8. A composition according to claim 7 and further defined by said effective amount of at least one protease enzyme inhibiting agent being present in said composition in amounts sufficient to provide combined concentration thereof from approximately 10 picograms per milliliter of said composition to approximately 10 milligrams per milliliter of said composition.

9. A composition according to claim 7 and further defined by said effective amount of at least one protease enzyme inhibiting agent being present in said composition in amounts sufficient to provide combined concentration thereof from approximately 1 nanogram per milliliter of said composition to approximately 1 milligram per milliliter of said composition.

10. A composition according to claim 13 wherein said effective amount of at least one protease enzyme inhibiting agent includes at least one protease enzyme inhibiting agent which is selected from the group consisting of: protease enzyme inhibitors of the serine class of proteases; protease enzyme inhibitors of the cysteine class of proteases; protease enzyme inhibitors of the aspartyl class of proteases; protease enzyme inhibitors of the metallo class of proteases; protease enzyme inhibitors of the carboxy-peptidase class of proteases; protease enzyme inhibitors of the trypsin class of proteases; protease enzyme inhibitors of the chymotrypsin class of proteases; protease enzyme inhibitors of the pancreatic proteases; protease enzyme inhibitors of the elastase class of proteases; protease enzyme inhibitors of the Bowman Birk inhibitor family; protease enzyme inhibitors of the potato inhibitor 1 family.

11. A composition according to claim 10 and further defined by said effective amount of at least one protease enzyme inhibiting agent being present in said composition in amounts sufficient to provide combined concentration thereof from approximately 10 picograms per milliliter of said composition to approximately 10 milligrams per milliliter of said composition.

12. A composition according to claim 10 and further defined by said effective amount of at least one protease enzyme inhibiting agent being present in said composition in amounts sufficient to provide combined concentration thereof from approximately 1 nanogram per milliliter of said composition to approximately 1 milligram per milliliter of said composition.

13. A method for treating skin to reduce the risk of skin cancer induced by sunlight or ultraviolet radiation, comprising:
    applying an effective amount of at least one protease enzyme inhibiting agent to the skin in a suitable, non-carcinogenic topical vehicle to reduce concentration of at least one proteolytic enzyme present in the skin being treated.

14. A method according to claim 13 and further defined by applying said effective amount of at least one protease enzyme inhibiting agent in said topical vehicle in amounts sufficient to provide a combined concentration from approximately 10 picograms per milliliter to approximately 10 milligrams per milliliter of said at least one protease enzyme inhibiting agent in said topical vehicle.

15. A method according to claim 13 and further defined by applying said effective amount of at least one protease enzyme inhibiting agent in said topical vehicle in amounts sufficient to provide a combined concentration from approximately 1 nanogram per milliliter to approximately 1 milligram per milliliter of said at least one protease enzyme inhibiting agent in said topical vehicle.

16. A method according to claim 13 wherein said effective amount of at least one protease enzyme inhibiting agent is applied in said topical vehicle with at least one suitable ultraviolet sunscreen agent which is present in amounts sufficient to reduce the amount of ultraviolet radiation striking skin so treated.

17. A method according to claim 16 wherein said effective amount of at least one protease enzyme inhibiting agent is selected from the group consisting of: protease enzyme inhibitors of the serine class of proteases; protease enzyme inhibitors of the cysteine class of proteases; protease enzyme inhibitors of the aspartyl class of proteases; protease enzyme inhibitors of the metallo class of proteases; protease enzyme inhibitors of the carboxy-peptidase class of proteases; protease enzyme inhibitors of the trypsin class of proteases; protease enzyme inhibitors of the chymotrypsin class of proteases; protease enzyme inhibitors of the pancreatic proteases; protease enzyme inhibitors of the elastase class of proteases; protease enzyme inhibitors of the Bowman Birk inhibitor family; protease enzyme inhibitors of the potato inhibitor 1 family.

18. A method according to claim 17 wherein said applying is accomplished using an effective amount of at least one protease enzyme inhibiting agent which is present in said topical vehicle in amounts sufficient to provide combined concentration of said at least one protease enzyme inhibiting agent from approximately 10 picograms per milliliter to approximately 10 milligrams per milliliter of resulting combined topical vehicle and inhibiting agent.

19. A method according to claim 17 wherein said applying is accomplished using an effective amount of at least one protease enzyme inhibiting agent which is present in said topical vehicle in amounts sufficient to provide combined concentration of said at least one protease enzyme inhibiting agent from approximately 1 nanogram per milliliter to approximately 1 milligrams per milliliter of resulting combined topical vehicle and inhibiting agent.

20. A method according to claim 13 wherein said effective amount of at least one protease enzyme inhibiting agent is selected from the group consisting of: protease enzyme inhibitors of the serine class of proteases; protease enzyme inhibitors of the cysteine class of proteases; protease enzyme inhibitors of the aspartyl class of proteases; protease enzyme inhibitors of the metallo class of proteases; protease enzyme inhibitors of the carboxy-peptidase class of proteases; protease enzyme inhibitors of the trypsin class of proteases; protease enzyme inhibitors of the chymotrypsin class of proteases; protease enzyme inhibitors of the pancreatic proteases; protease enzyme inhibitors of the elastase class of proteases; protease enzyme inhibitors of the Bowman Birk inhibitor family; protease enzyme inhibitors of the potato inhibitor 1 family.

21. A method according to claim 20 wherein said applying is accomplished using an effective amount of at least one protease enzyme inhibiting agent which is present in said topical vehicle in amounts sufficient to provide combined concentration of said at least one protease enzyme inhibiting agent from approximately 10 picograms per milliliter to approximately 10 milligrams per milliliter of resulting combined topical vehicle and inhibiting agent.

22. A method according to claim 20 wherein said applying is accomplished using an effective amount of at least one protease enzyme inhibiting agent which is present in said topical vehicle in amounts sufficient to provide combined concentration of said at least one protease enzyme inhibiting agent from approximately 1 nanogram per milliliter to approximately 1 milligrams per milliliter of resulting combined topical vehicle and inhibiting agent.

* * * * *